US011478785B2

(12) United States Patent
Fitzer et al.

(10) Patent No.: US 11,478,785 B2
(45) Date of Patent: Oct. 25, 2022

(54) LABORATORY CABINET DEVICE FOR STORING LABORATORY SAMPLES WITH A MAGNETIC CLOSURE

(71) Applicant: Eppendorf AG, Hamburg (DE)

(72) Inventors: Jan Fitzer, Hamburg (DE); Gregor Bechmann, Hamburg (DE); Arne Schafrinski, Hamburg (DE); Sören Mensch, Hamburg (DE)

(73) Assignee: EPPENDORF SE, Hamburg (DE)

( * ) Notice: Subject to any disclaimer, the term of this patent is extended or adjusted under 35 U.S.C. 154(b) by 0 days.

(21) Appl. No.: 16/981,266

(22) PCT Filed: Mar. 14, 2019

(86) PCT No.: PCT/EP2019/056466
§ 371 (c)(1),
(2) Date: Sep. 15, 2020

(87) PCT Pub. No.: WO2019/175337
PCT Pub. Date: Sep. 19, 2019

(65) Prior Publication Data
US 2021/0023549 A1    Jan. 28, 2021

(30) Foreign Application Priority Data
Mar. 16, 2018   (EP) .................................. 18162376

(51) Int. Cl.
*B01L 1/00* (2006.01)
*A47B 81/00* (2006.01)
*E05F 5/06* (2006.01)

(52) U.S. Cl.
CPC ............... *B01L 1/00* (2013.01); *A47B 81/00* (2013.01); *E05F 5/06* (2013.01); *B01L 2300/041* (2013.01)

(58) Field of Classification Search
CPC ... B01L 1/00; A47B 81/00; E05F 5/06; E05C 17/56; E05C 19/16
USPC ................ 312/209, 401; 292/DIG. 33, 251.5
See application file for complete search history.

(56) References Cited

U.S. PATENT DOCUMENTS

| 2,812,203 | A |   | 11/1957 | Scholten |          |
|-----------|---|---|---------|----------|----------|
| 2,955,239 | A | * | 10/1960 | Rouse    | H01F 7/0252 |
|           |   |   |         |          | 211/DIG. 1 |
| 3,079,535 | A | * | 2/1963  | Schultz  | H01F 7/0226 |
|           |   |   |         |          | 335/295  |
| 4,235,493 | A | * | 11/1980 | Bridges  | E05D 5/065 |
|           |   |   |         |          | 312/265.3 |
| 5,040,857 | A | * | 8/1991  | Mandel   | E05D 3/022 |
|           |   |   |         |          | 312/405  |

(Continued)

FOREIGN PATENT DOCUMENTS

| CN | 203034971 U | 7/2013  |
| CN | 205638019 U | 10/2016 |

(Continued)

*Primary Examiner* — James O Hansen
(74) *Attorney, Agent, or Firm* — Todd Lorenz

(57) ABSTRACT

The invention relates to a laboratory cabinet device for storing laboratory samples with a magnetic closure for the door. It concerns in particular a tempering cabinet for tempering laboratory samples, in particular an incubator for the growth of cell cultures. The magnetic closure works with magnetic elements arranged without contact in the closing position.

7 Claims, 9 Drawing Sheets

(56) References Cited

U.S. PATENT DOCUMENTS

| | | | |
|---|---|---|---|
| 5,076,623 A * | 12/1991 | Richards | E05B 47/0038 |
| | | | 292/201 |
| 5,782,512 A | 7/1998 | Cargnoni | |
| 2009/0021333 A1 | 1/2009 | Fiedler | |
| 2011/0006652 A1 * | 1/2011 | Veltrop | F25D 23/087 |
| | | | 277/345 |
| 2014/0042756 A1 * | 2/2014 | Browne | E05C 19/16 |
| | | | 292/251.5 |
| 2014/0054904 A1 | 2/2014 | Andrews | |

FOREIGN PATENT DOCUMENTS

| | | | |
|---|---|---|---|
| CN | 206144341 U | 5/2017 | |
| EP | 0238313 A1 | 9/1997 | |
| EP | 1700983 B1 | 7/2008 | |
| GB | 1009996 | 11/1965 | |
| GB | 2395744 | 6/2004 | |
| JP | 2012-102525 A | 5/2012 | |
| WO | WO 2013/057344 A1 | 4/2013 | |
| WO | WO 2015182119 | * 12/2015 | E05C 19/16 |

* cited by examiner

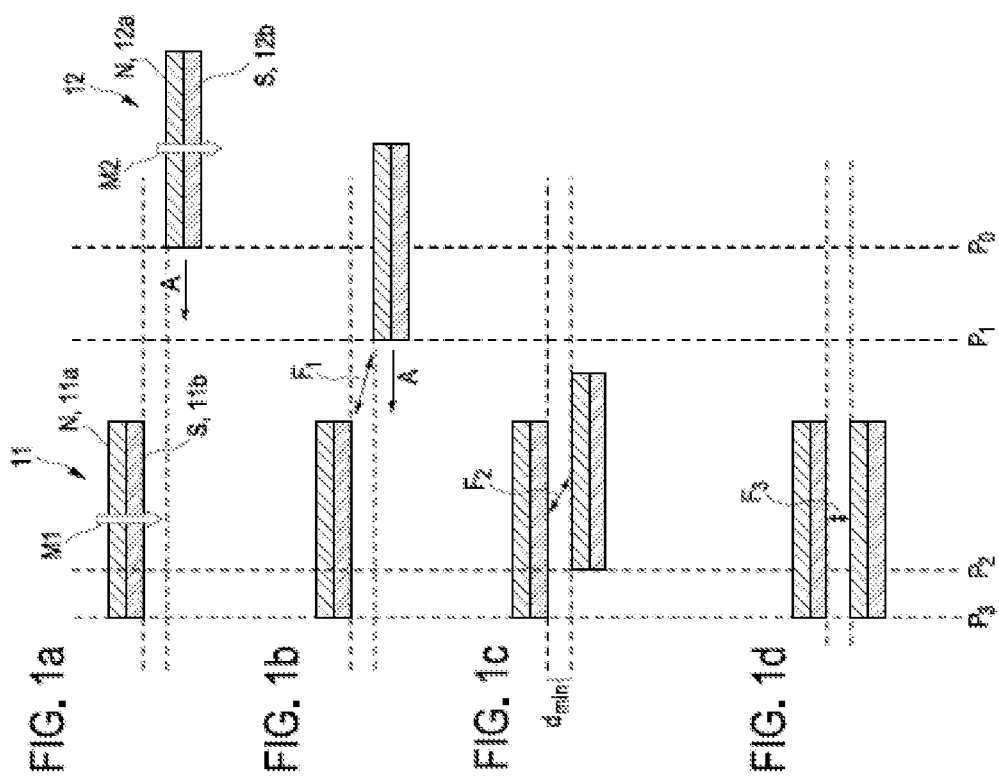

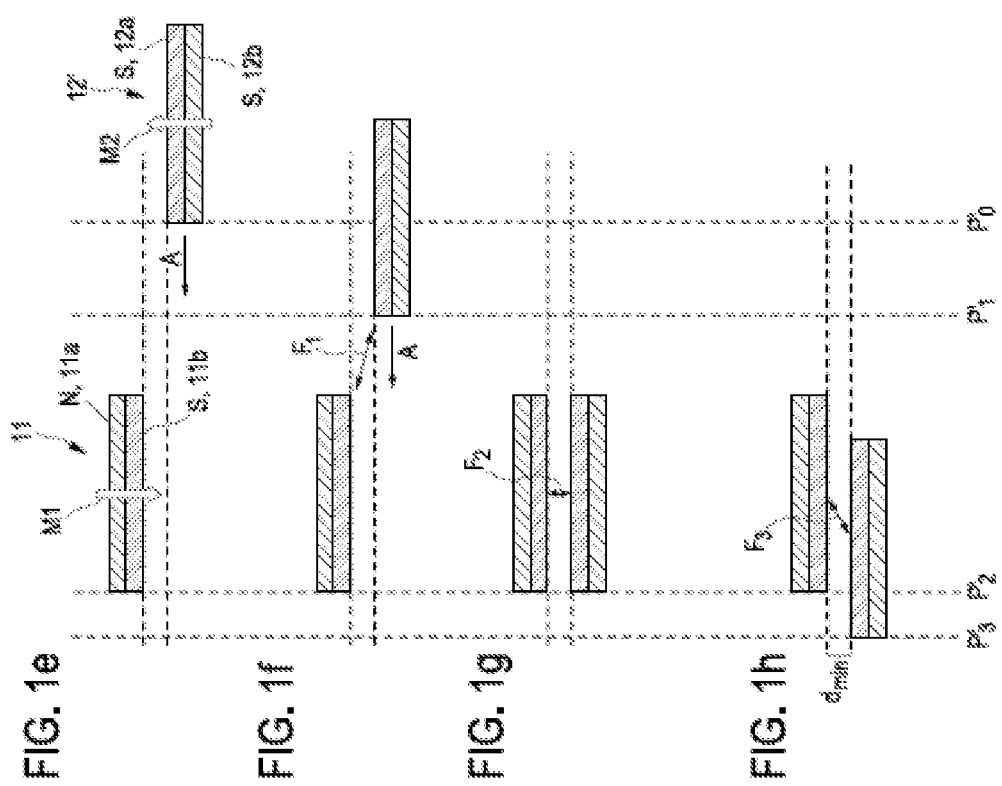

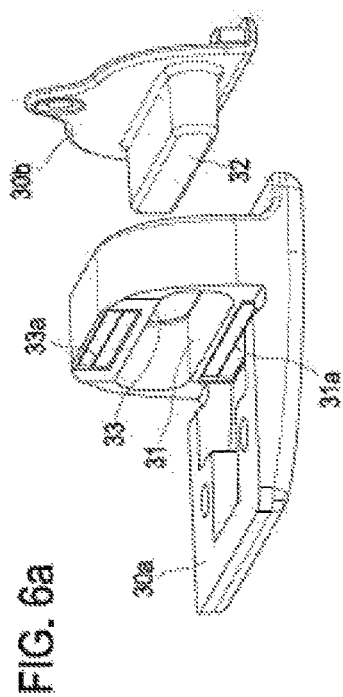
FIG. 6a
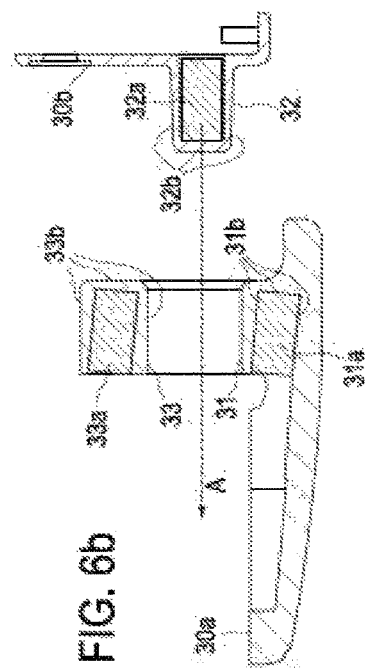
FIG. 6b
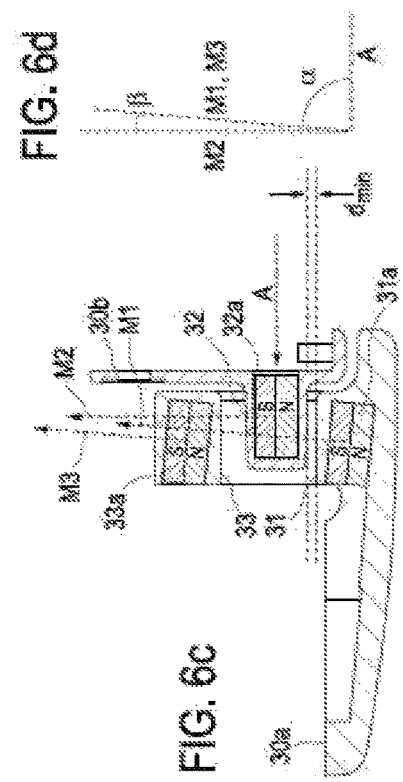
FIG. 6c
FIG. 6d

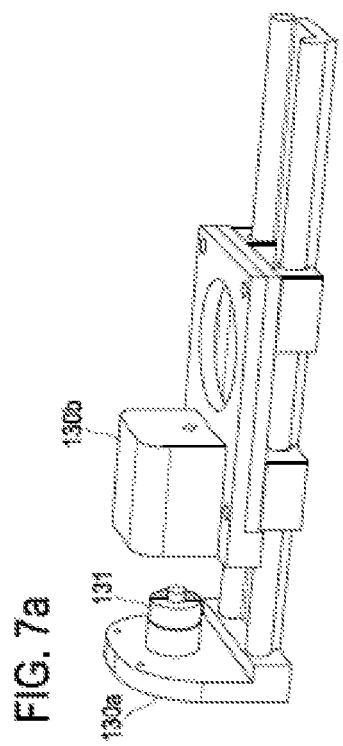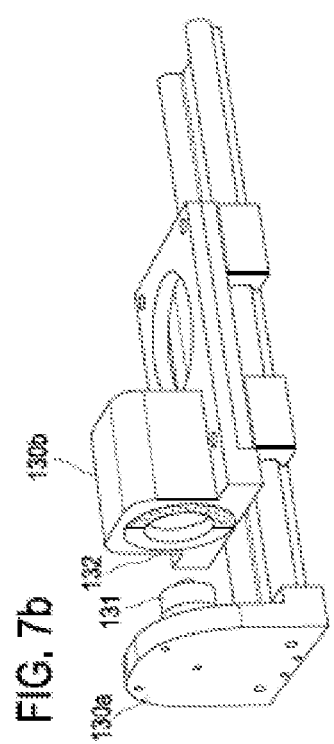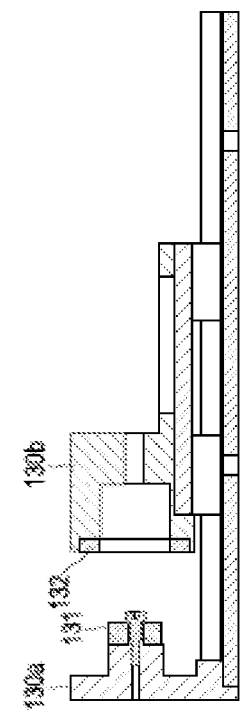

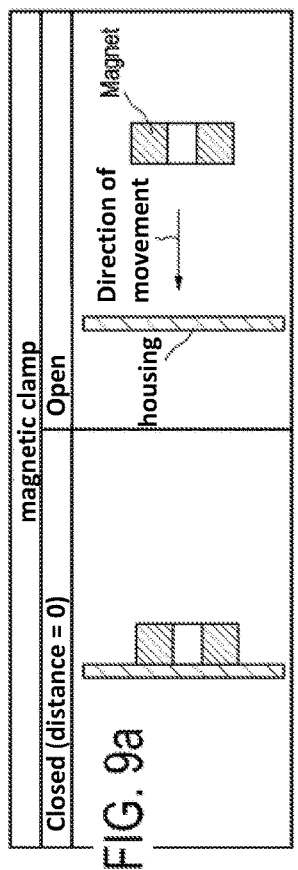
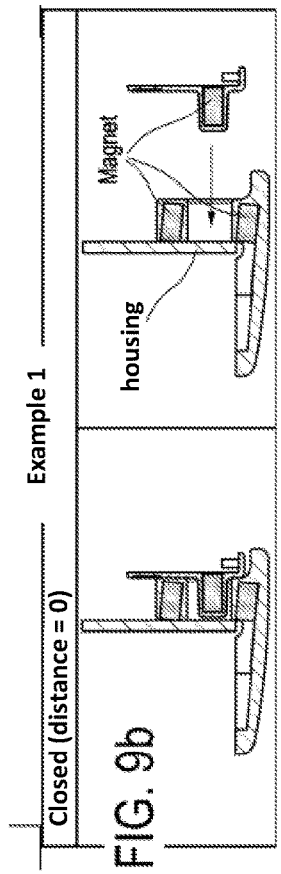
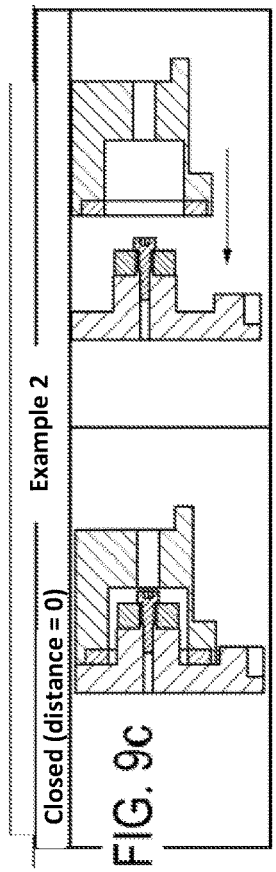

LABORATORY CABINET DEVICE FOR STORING LABORATORY SAMPLES WITH A MAGNETIC CLOSURE

The invention relates to a laboratory cabinet device for storing laboratory samples with a magnetic closure for the door. It concerns in particular a tempering cabinet for tempering laboratory samples, in particular an incubator for the growth of cell cultures.

Such incubators are used in biological and medical laboratories to keep cells in cell culture under controlled environmental conditions, thus enabling the growth of living cells in vitro. For this purpose, the temperature and the gas composition or the humidity of the atmosphere inside an incubator chamber isolated from the environment are kept at the desired values by the apparatus devices of the incubator. Eukaryotic cells must be cultivated in CO2 incubators. The atmosphere is formed by air with a certain CO2 and O2 content and a certain humidity, a suitable temperature is often 37° C. Such temperature control cabinets have a housing surrounding the incubator chamber, for example an outer housing, with a housing opening through which the user stores and removes the samples inside the housing, especially in the incubator chamber. The housing door should reliably close the inside of the housing where the incubator chamber is located. For this purpose, various technical solutions are known in the prior art. Mechanically acting closures have, for example, a bolt closure, a tension closure or a latch closure, which must be unlocked to open. Such mechanical solutions are complex and generate mechanical vibrations on the housing, which continue into the chamber where the samples (eukaryotic cells) are stored. Magnetically acting closures, as they are known in particular from refrigerator closures, generate a mechanical vibration when the door is closed or opened due to a high magnetic holding force, which can also continue into the chamber. As laboratory samples are often sensitive and of high value, it is desirable that opening and closing the housing door avoids mechanical shock or vibration of the housing, as this can continue into the incubator chamber containing the sensitive samples.

It is therefore an object of the present invention to provide an improved laboratory cabinet device.

The invention solves this problem by the laboratory cabinet device according to claim 1. Preferred embodiments are, in particular, subjects of the dependent claims.

The magnetically acting holding device for holding the housing door in the closed position according to the invention offers the advantage that due to the contact-free arrangement of the first and second holding elements, their adhesion is avoided and therefore no or only slight vibration or no or only slight jerk is generated when opening the housing door. As a result, no vibration is transmitted to the laboratory samples located inside the housing, especially those in the incubator chamber, which allows the laboratory cabinet device to be used with trouble-free storage of the laboratory samples. At the same time, the operability of the laboratory cabinet device benefits from the properties of the magnetic field. The magnetic force is approximately proportional to the inverse square of the distance between the magnetic partners acting together. In a certain relative position of the housing door to the housing or of the first and second holding elements, the magnetic force will automatically close the housing door and reliably transfer it to the locking position without the user having to ensure this movement and without the user—or any mechanics—having to effect any separate locking process. Since the magnetic elements do not touch each other, the jerky opening of magnets adhering to each other is avoided, which can be found in some prior art magnetic closures. The holding device replaces in particular mechanical locking devices or interlocks. Due to the contactless interaction, wear of the holding device, which is caused by contact, is avoided. These features make the operation of the housing door and thus of the laboratory cabinet device particularly safe and convenient. The holding device can be optimally integrated into the laboratory cabinet device, since the space required for the holding device on the laboratory cabinet device is relatively small.

The laboratory cabinet device for storing laboratory samples is especially a temperature control cabinet for tempering laboratory samples, especially a CO2 incubator. Such devices are electrically operated and have a voltage connection. The holding device preferably works with one or more permanent magnets, so that the holding device is independent of the power supply. The closure of the housing door is therefore guaranteed even if the power supply fails.

The temperature control cabinet regulates the temperature of the laboratory samples, i.e. it keeps the inside of the housing and thus the laboratory samples stored there within the scope of tolerances by means of temperature control at a setpoint temperature that, in particular, can be set by the user. This can be above room temperature (ambient temperature), as is the case with a warming cabinet or incubator, or below room temperature, as is the case with a refrigerator or freezer. In the case of a laboratory cabinet designed as a climatic cabinet, a climate parameter characterizing the inside of the cabinet is preferably also controlled within tolerances. This climate parameter can be the humidity of the air and/or a gas concentration, e.g. a CO2, O2 and/or N2 concentration. Such a climate chamber is for example an incubator for laboratory samples consisting of living cell cultures.

The housing of the laboratory cabinet device is preferably an external housing whose housing walls are in contact with the environment. However, the housing can also be an inner housing located within an outer housing. For example, an incubator may have at least one chamber serving as the inner housing, which can be closed by at least one housing door or chamber door. The housing door may accordingly be an outer housing door which, in the closed position, adjoins the surroundings, or may be an inner housing door to which, in particular, an additional outer housing door may be provided, only the latter adjoining the surroundings in the closed position and wherein the inner housing door, in the closed position of the outer housing door, is situated in a cavity between the inner housing, the outer housing and the outer housing door.

The housing door comprises, in particular, a hinge device, which connects the housing door to the housing in a pivoting manner. Such a swing door is moved by a rotation between an open position and the closing position. The hinge device may, in particular, be located at the—in the intended use of the laboratory cabinet device—vertically oriented outer edge of a cuboid housing, which is adjacent to the housing opening. The base plate of a cuboidal housing is arranged horizontally when the laboratory cabinet device is used as intended, the side walls of the housing are arranged in particular vertically, and the top plate of the housing is arranged horizontally, opposite the base plate, in particular. The holding device is preferably arranged on an outer edge of the housing on which the hinge device is not located, preferably in the closed position opposite the hinge device, i.e. in particular on the edge adjacent to the housing opening.

However, a holding device may also be alternatively or additionally arranged at another outer edge of the housing, in particular a horizontally running outer edge.

The housing door can also be a sliding door, which is moved by a translatory movement between an open position and the closing position. A mixed swivel/translatory movement of the housing door is also possible.

The laboratory cabinet device may comprise more than one holding device, each comprising, as defined, the holding elements which interact magnetically with each other in the closed position of the cabinet door. In the case of several holding devices, these are preferably arranged at a distance from each other in the closed position. In particular, they may be located on the same outer edge of the housing or on different outer edges of the housing. By providing several holding devices, the uniform closing of the housing door and the distribution of the closing forces, which are acting between the door and the housing, can be optimized.

Preferably, the several holding devices are configured in an identical manner, consisting of at least a first and a second holding element. However, it may also be provided that the multiple holding devices are designed in different ways, consisting of at least a first and a second holding element. In this way, the locking characteristics of the housing door, i.e. the force between the housing and the housing door, caused by the holding devices, applied against the deflection of the housing door from the closing position, can be influenced in the desired manner.

In the closing position, the housing door preferably seals the inside of the housing tightly, which is achieved, in particular, by at least one sealing device of the housing door and the frame of the housing opening, respectively. The seal is preferably used to achieve a sealing effect sufficient for the high requirements of incubating living cell cultures. Since certain gas concentrations and the temperature inside the incubator are controlled, a good seal ensures cost-effective operation. However, the invention also concerns laboratory cabinet devices with a housing which does not completely seal the inside of the housing from the environment.

The group of magnetically acting holding elements comprises a first holding element, which is arranged on the housing, in particular, which is fixed there as a separate component or is integrated there, and a second holding element, which is arranged on the housing door, in particular, which is fixed there as a separate component or is integrated there.

The group of magnetically acting holding elements preferably comprises exactly two holding elements, and preferably exactly three holding elements, as explained below. However, it is equally preferred that the group of magnetically acting holding elements contains more than two or three holding elements. The magnetic effect of the holding elements is based on the fact that at least one holding element is configured as a magnetic element by comprising at least one magnet or consisting of at least one magnet. In a particularly preferred embodiment this is a permanent magnet. But it can also be an electromagnet.

Preferably, the group of magnetically acting holding elements comprises a magnetic element and, in particular, a magnetic element complementary to it for forming the magnetic attraction force, in particular by means of ferromagnetism. A holding device may comprise several magnetic elements, which generate the desired magnetic force, in particular 2, 3, 4, 5, 6 magnetic elements or any other number. With such a configuration, the closure characteristics can be precisely adjusted and released again with precisely defined holding forces.

A holding element or magnetic element is preferably a separate component that is attached to the housing and/or the housing door when the laboratory cabinet device is installed. A holding element or magnetic element can also be an integral part of the housing and/or the housing door.

A magnetic element is preferably a permanent magnet or comprises one. Preferably the magnet comprises a cover element to protect it from mechanical damage or corrosion.

Preferably, the permanent magnet is made of or comprises a samarium-cobalt alloy. These materials have proven to be particularly resistant to corrosion in humid or chemical laboratory environments. However, it is also possible to use other permanent magnets, such as neodymium-iron magnets.

Preferably, the laboratory cabinet device comprises at least one elastic element which, in the closed position, is arranged between the housing and the housing door and, especially in the closed position between the housing and the housing door, is compressed by the holding force of the holding device. The elastic element serves, in particular, as a stop for the housing door on the housing, which mechanically cushions and dampens the contact of the housing door on the housing. In addition, the elastic element serves as an abutment for the holding force of the holding device, which compresses the elastic element in the closing position. When used with an elastic element, the holding device of the laboratory cabinet device according to the invention offers the advantage that the range of the magnetic force compensates for manufacturing variations of the dimensions or of the elasticity of the elastic element, so that a certain independence of the holding force and thus of the reliability of the closure from these properties of the elastic element is achieved.

The elastic element is in particular a seal which, in the closed position, hermetically separates the inside of the housing from the environment. In particular, the seal is located on an outer wall of the housing, which also comprises the housing opening. The seal preferably runs continuously around the housing opening. Alternatively or additionally, such a seal can be arranged on the inside of the housing door in such a way that it runs continuously around the housing opening in the closed position. The seal is preferably made of silicone or preferably consists of silicone. The silicone can be a silicone foam and/or comprises cavities and/or recesses. Through such pores or cavities the desired elasticity or the thermal insulation capacity of the seal is achieved.

The closing position is particularly characterized in that the interior of the housing is closed by the housing door, in particular tightly closed, and in particular closed by means of a seal for the purpose of incubating living cell cultures. In the closed position, the elastically deformable element or seal is elastically deformed by the magnetic holding force of the holding device.

The first and the second holding elements are arranged and configured to hold the housing door by the magnetic force in the closed position without contacting it. The first and second holding elements do not touch each other in the closed position and/or preferably do not touch each other during the closing movement of the housing door. In particular, two magnetic partners (magnetic partner: permanent magnet or component made of ferromagnetic material) of the holding device do not touch each other in the closed position and/or preferably do not touch each other during the closing movement of the housing door. It is possible that in the closed position between the magnetic partners a spacer element is provided, which prevents contact between the magnetic partners in the closed position and/or on which the first and second holding elements support each other. The spacer element can be located on the housing door or on the housing.

Preferably, the first and second holding elements are spaced apart in the closing position so that their minimum distance $d_{min}$ in the closing position is greater than zero. The minimum distance $d_{min}$ is the smallest distance between the first and second holding element in their mounting or construction position on the laboratory cabinet device when the cabinet door is in the closed position. This minimum distance can be given, in particular, by a gap formed between the first and second holding element in the closing position. This gap can be formed by a cuboidal or layered clearance between the first and second holding elements in the closed position or may consist of this clearance. The distance $d_{min}$ is preferably 0 mm<$d_{min}$<10.0 mm, preferably 0 mm<$d_{min}$<5.0 mm, preferably 0 mm<$d_{min}$<3.0 mm, preferably 0 mm<$d_{min}$<1.0 mm, preferably 0 mm<$d_{min}$<0.5 mm. With such a minimum distance a sufficient magnetic holding force can be realized.

Preferably at least one holding element of this group of holding elements comprises a permanent magnet and at least one other holding element of this group comprises a material magnetically interacting with this permanent magnet. Preferably the first holding element comprises a permanent magnet and the second holding element comprises a material magnetically interacting with this permanent magnet. Preferably, the second holding element comprises a permanent magnet and the first holding element comprises a material magnetically interacting with this permanent magnet. In particular, this material can be configured as a section of the enclosure door or of the housing. A permanent magnet has a constant magnetic field. The magnetic force exerted by such a permanent magnet depends on the magnetic partner interacting with it, which can also be a permanent magnet or a ferromagnetic material. In the case of two interacting permanent magnets, the magnetic force can be attractive or repulsive depending on the polarity and orientation of the permanent magnets. The magnetic force between the magnetic partners depends not only on the respective solid state properties or magnetic fields, but also on the geometric position of the magnetic partners relative to each other. The present invention makes use of this in order to achieve the desired magnetic force by positioning and aligning the magnetic partners to each other, especially in the closing position. When the housing door is in the closing position, the magnetic force then acting is called closing force. This force holds the housing door in the closing position in the desired manner, i.e. with the desired force, and thus counteracts opening.

Preferably, at least one holding element of this group of holding elements comprises a first permanent magnet and at least one further holding element of this group comprises a second permanent magnet magnetically interacting with this first permanent magnet. Preferably, at least one holding element of this group of holding elements comprises a first permanent magnet and at least one further holding element of this group comprises a second permanent magnet magnetically interacting with this first permanent magnet. The first and second permanent magnets are preferably arranged with the same polarity in the closing position, so that there is an attracting effect between the first and second permanent magnet. The first and the second permanent magnet can also be arranged with opposite polarity in the locking position, so that there is a repelling effect between the first and the second permanent magnet.

Preferably, the first and second holding elements are arranged against each other in such a way that, when the housing door is closed, they reach the locking position by a closing movement that moves the first and second holding elements parallel to each other. This parallel movement prevents contact. In addition, such a parallel or almost parallel movement can be achieved with both a rotating and a sliding housing door.

Preferably the first and/or the second holding element comprise a permanent magnet, which has a magnetic axis M extending along a magnetic north-south pole direction, wherein the closing movement on reaching the closing position preferably runs perpendicularly to the magnetic axis, and in a further preferred embodiment the closing movement on reaching the closing position runs at an angle to the magnetic axis, wherein preferably $70°<=\alpha<90°$, preferably $80°<=\alpha<90°$, $83°<=\alpha<=87°$, preferably $\alpha=90°$.

In particular, this magnetic axis can be perpendicular to a surface, especially to the largest surface of a magnetic element. This arrangement allows a magnetic force to build up over a longer movement distance. The maximum magnetic force is reached when the magnetic partners, in particular the first and second holding elements are directly opposite each other, i.e. when in particular their central component axes or central magnetic axes M coincide.

Preferably, the group of holding elements comprise at least one cuboid permanent magnet whose north-south pole direction (magnet axis) extends perpendicular to the largest area of the cuboid permanent magnet. The magnetic axis is preferably perpendicular to or at the specified angle $\alpha$ to the closing movement with which the housing door reaches its end position (closing position) on the housing. The largest area thereby defines the area over which an increasing magnetic force is built up with increasing closing.

Preferably a first relative position of the first and the second holding elements is provided in which they exert a first attractive magnetic force on each other and preferably a second relative position of the first and the second holding elements is provided in which they exert another, second attractive magnetic force on each other, which is, in particular, greater than the first magnetic force. The first and the second holding elements are then preferably arranged against each other in such a way that, when closing the housing door from the open position, they first reach the first relative position, as shown as an example in FIGS. 1a and 1b, and then reach the closing position in which the second relative position is present, as shown as exemplary in FIG. 1c. This automatically pulls the housing door from the first relative position to the second relative position.

Preferably, the laboratory cabinet device has an elastic element, which is compressed in the closed position by the cabinet door means this magnetic force. A third relative position of the first and second holding elements is preferably provided, in which the elastic element is compressed more strongly than in the second relative position, in that the first and second holding elements exert a third attractive magnetic force on each other in the third relative position, which is greater than the second magnetic force. In this way a tolerance in the dimensioning of the components of the laboratory cabinet device is achieved, since the attracting interaction is also guaranteed if the elastic element or the seal is somewhat thicker than defined by the target specification due to scattering during production or during installation or replacement in the laboratory cabinet device. Even age-related fluctuations of the elastic element or a seal can be compensated in this way.

Preferably, the first and second holding elements have the same predetermined distance in the second and third relative positions. The third magnetic force acting in the third relative position is preferably the maximum achievable magnetic force between the first and second holding element at this distance. This maximum magnetic force is achieved, in particular, when the magnetic partners, especially the first and second holding elements, are directly opposite each other, i.e. when, in particular, their central component axes or their central magnetic axes M coincide. This is illustrated by the third relative position as shown exemplary in FIG. 1d.

Preferably a first relative position of the first and of the second holding elements is provided, in which they exert a first repulsive magnetic force on one another, and preferably a second relative position of the first and of the second holding elements is provided, in which they exert a second repulsive magnetic force on one another, which is in particular greater than the first magnetic force, and preferably a third relative position of the first and of the second holding elements is provided, in which they exert a third repulsive magnetic force on one another, which is in particular less than the second magnetic force. Preferably, the first and the second holding elements are arranged against each other in such a way that when the housing door is closed, they first reach the first relative position, then in the further course of the closing movement they reach the second relative position and after that the closing position, in which the third relative position is present. By this arrangement, the housing door, preferably in the presence of the elastic element between the housing door and the housing, is forced into the closing position by a repulsive magnetic force and is thus held in the closing position. An embodiment with a holding force based on repulsive magnetic forces is illustrated using FIGS. 1e to 1h exemplary.

Preferably, the group of holding elements comprises at least one ring-shaped or hollow cylindrical permanent magnet whose north-south pole direction (first magnet axis) extends perpendicular to the central geometric axis running through the opening of the ring-shaped or hollow cylindrical permanent magnet. The geometrical axis is, in particular, the axis of symmetry of the ring-shaped or hollow cylindrical permanent magnet. The magnetic partner of this ring-shaped or hollow cylindrical permanent magnet is preferably a second ring-shaped or hollow cylindrical permanent magnet, which can be inserted into the opening of the first ring-shaped or hollow cylindrical permanent magnet. Wherein, the north-south pole direction (second magnet axis) of the second permanent magnet runs parallel to the first magnet axis. Depending on whether the polarity of the first and second permanent magnets is in the same direction or in the opposite direction, the coaxial and centered position of the first and second permanent magnets, in which they are completely pushed together, results in a rest position or a reversal point.

If the magnetic axes of the first and of the second ring-shaped or hollow cylindrical permanent magnets are in the same direction, as shown in FIG. 3a exemplary, there is first a repulsion, when the first and second ring-shaped or hollow cylindrical permanent magnets are pushed together along the geometrical axis, then a reversal point and then an attraction until the geometrically centered position is reached—corresponding to a rest position there. A further deflection from this rest position in the same direction along the geometric axis would then initially occur against the attracting force and would then be accelerated from a further reversal point by a repulsion. A holding device can be configured so that the closing position corresponds to the geometrically centered position or to a position in which the second permanent magnet partially overlaps the first permanent magnet in the axial sliding direction and the permanent magnets attract each other.

If the magnetic axes of the first and second ring-shaped or hollow cylindrical permanent magnets are in opposite directions, as shown exemplary in FIG. 3b, when the first and second ring-shaped or hollow cylindrical permanent magnets are pushed together along the geometrical axis, there is initially an increasing repulsion in this direction until the geometrically centered position is reached—corresponding to a reversal point there. A further deflection from this reversal point position in the same direction along the geometric axis is then initially accelerated by the repelling force, which decreases in this direction. A holding device may be configured so that the closing position corresponds to a position in which the second permanent magnet has passed the reversal point in the closing direction and partially overlaps with the first permanent magnet in the axial sliding direction and the permanent magnets repel each other.

The magnetic partner of the ring-shaped or hollow cylindrical permanent magnet can also be a ferromagnetic component if the repulsion principle is used.

Preferably, the at least one permanent magnet is a component of a holding element of the group of holding elements and in particular a component of a magnetic element. This holding element preferably comprises a cover element or a socket, of which at least one permanent magnet is partially or completely enclosed, whereby preferably this socket is not subjected to pressure from another holding element when the housing door is closed. However, it is also possible that the cover element or socket serves as a spacer element, which in the closing position is pressurized by another holding element.

Preferably, the group of holding elements comprises a third magnetically acting holding element, which is arranged on the housing or on the housing door and which, with the first and second holding element, generates the magnetic force with which the housing door is held in the closed position on the housing. The closure characteristics can be influenced in the desired way by a third holding element.

Preferably, the first and the third holding elements are spaced apart and parallel to each other in such a way that a free space is formed between them, in which the second holding element engages in the closing position. This results in the advantage of low mechanical stress on the holding elements during closing and opening. Preferably, the second and the third holding elements are spaced apart and arranged in parallel so that a free space is formed between them in which the first holding element engages in the closing position. This configuration has the advantage that the holding element, which is placed between two other holding elements in the closing position, experiences a vanishing net force in the direction of the magnetic polarity, because it is held from both sides along the direction of the magnetic polarity by neutralizing forces.

In a preferred embodiment, the holding elements are arranged parallel to each other in the closed position or have outer surfaces running parallel to each other. In preferred design, the magnetic elements of these holding elements are arranged in such a way that their magnetic axes M form an angle $\beta$ to each other, wherein, in particular $\beta=90°-\alpha$. The angle $\alpha$ was explained above. By "adjusting" one magnetic element relative to the other magnetic element, the magnetic force or closing force acting near the closing position during closing/opening can be influenced in the desired way.

Further preferred embodiments of the laboratory cabinet device according to the invention can be found in the description of the embodiments according to the figures.

It shows:

FIGS. 1a, 1b, 1c and 1d show, in different relative positions, the first and second holding element of a holding device whose holding force is based on attracting magnetic forces and which can be used in an embodiment of the laboratory cabinet device according to the invention.

FIGS. 1e, 1f, 1g and 1h show, in different relative positions, the first and second holding element of a holding device whose holding force is based on repulsive magnetic forces and which can be used in an embodiment of the laboratory cabinet device according to the invention.

FIGS. 2a, 2b, 2c and 2d each show, in a horizontal cross-section, an embodiment of the laboratory cabinet device according to the invention, in which the first and second holding elements are shown in the relative positions of FIGS. 1a, 1b, 1c and 1d.

Figure 3A:
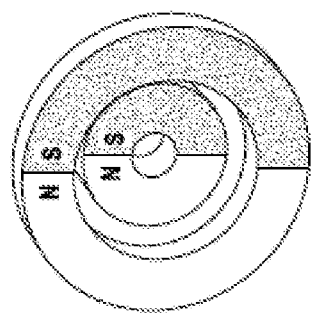
Figure 3B:
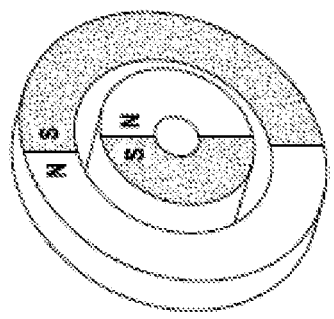

FIGS. 3a and 3b each show the first and second holding element of two holding devices, which can be used in a laboratory cabinet device according to further embodiments of the invention.

Figure 4:
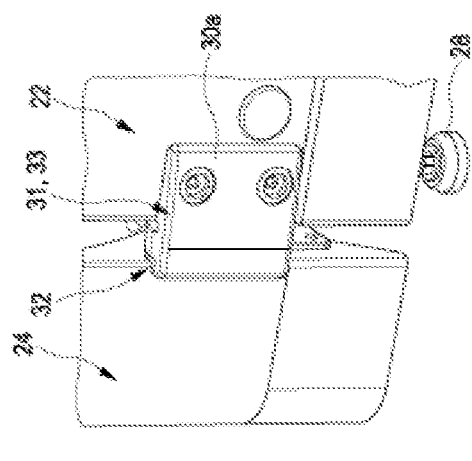

FIG. 4 shows, in a section, a perspective exterior view of an embodiment of a holding device on a laboratory cabinet device according to the invention, in the closed position of the cabinet door.

Figure 5:
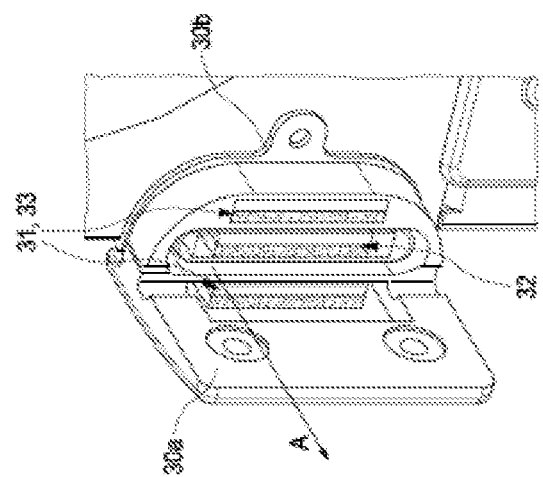

FIG. 5 shows the holding device of FIG. 4 from a viewpoint inside the housing, wherein the housing walls are hidden.

FIG. 6a shows a perspective exterior view of a holding device according to further embodiment, in the open position of the housing door.

FIG. 6b shows the holding device of FIG. 6a in cross-section, in the open position of the housing door.

FIG. 6c shows the holding device of FIG. 6b in a cross-section, in the closing position.

FIG. 6d shows the relative positions of the permanent magnets with magnet axes M1, M2 and M3 used in the example of FIGS. 6a to 6c with respect to the direction of movement A when closing the housing door or closure, using the angles α and β.

FIG. 7a shows a perspective exterior view of a holding device according to another embodiment, in the open position of the housing door.

FIG. 7b shows a second perspective outside view of the holding device of FIG. 7a, in the open position of the housing door.

FIG. 7c shows a cross-section of the holding device of FIGS. 7a and 7b, in the open position of the housing door.

Figure 8:
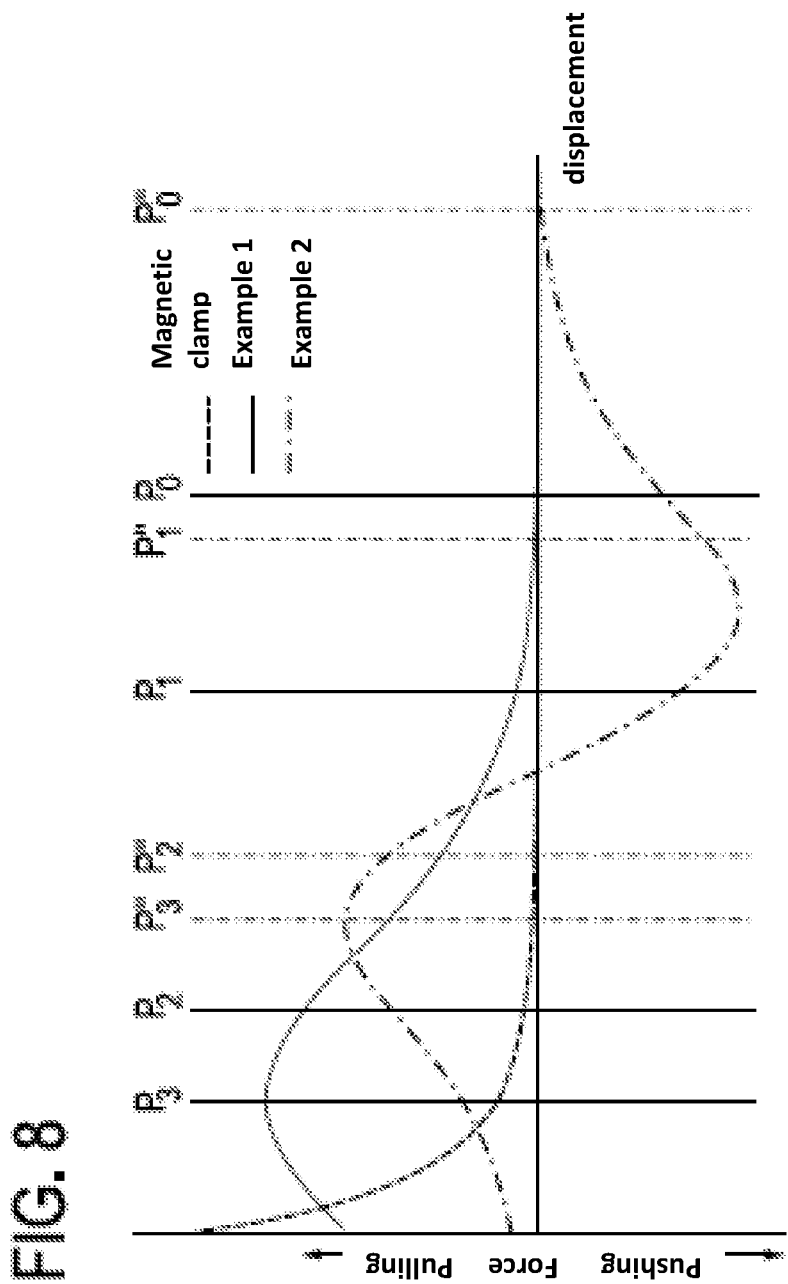

FIG. 8 shows a force-displacement diagram in which the force-displacement curves for the embodiments of FIGS. 6a to 6c are shown as "Example 1", the force-displacement curves for the embodiments of FIGS. 7a to 7c as "Example 2", and a comparative example with a conventional magnetic clamp closure.

FIG. 9a shows, in cross-sectional view and in closed and open position, a conventional magnetic clamp closure, to illustrate the "magnetic clamp" curve of FIG. 8.

FIG. 9b shows, in cross-sectional view and in a closed and open position, the closure from FIGS. 6a to 6c, to explain the curve "Example 1" in FIG. 8.

FIG. 9c shows, in cross-sectional view and in a closed and a open position, the closure from FIGS. 7a to 7c, to explain the curve "Example 2" in FIG. 8.

FIG. 1a shows the operating principle of the laboratory cabinet device according to the invention for the preferred case that the magnetic force acting in the closed position causes an attraction of the first holding element 11 and the second holding element 12. For this purpose, the first and second permanent magnets have the same polarity direction M1=M2, which results from the same relative position of north pole N and south pole S. The north pole is formed by the upper side 12a of the plate-shaped permanent magnet 12, the south pole by its lower side 12b. As shown in FIGS. 2a to 2d, the first holding element 11 is fixed by means of a support element 10 to the housing 2 of a laboratory cabinet device, here an incubator 1, and the second holding element 12 is attached to the housing door 4, which is rotatably mounted by means of a hinge 5 on a vertical outer edge of the housing adjacent to the housing opening 3. The group 11, 12, 13 of holding elements comprises a third magnetically acting holding element in FIGS. 2a to 2d, which is not shown in FIGS. 1a to 1d. This is fixed to the housing parallel to and at a distance from the first holding element 11 so that there is a gap between the first holding element 11 and the third holding element 13 in which the second holding element engages in the closing position P2. The three holding elements generate the magnetic force with which the housing door 4 is held in the closed position on housing 2. Thereby, the housing door 4 is pressed against the elastic seal 6 in the closed position. The elastic seal 6 runs around the housing opening 3 and is compressed in the closed position. The inside of the housing 7 is thus hermetically sealed in the closed position. The closing position is the relative position P2.

The housing door is open in the first relative position P0 shown in FIG. 1a. This position is called the opening position. The holding elements do not exert any effective magnetic force on each other.

In the first relative position P1 of the first holding element 11 and the second holding element 12 shown in FIG. 1b, exert a first attractive magnetic force F1 on each other, which moves the housing door automatically, i.e. without further user action, into the closed position. The closing movement A, with which the first and second holding element are moved into the closing position P2, is approximately a linear movement A due to the small closing angle BETA (see FIG. 2b) of the housing door relative to the housing front.

In the second relative position P2 of the first holding element 11 and the second holding element 12 shown in FIG. 1c, they exert a second attractive magnetic force F2 on each other, which is greater than the first magnetic force. In this position the housing door is closed (locked position) and the seal 6 is compressed so that the inside of the housing 7 is hermetically sealed against the environment. In this relative position P2, the centered position of the first and second holding elements is not yet reached, in which they are face centered against each other and the maximum magnetic force F3 acts. This centered position P3 would only be reached after the relative position P2 is reached, if the closing movement A is continued. However, since in the relative position P2 the opposing magnetic force and the restoring force of the elastically deformable sealing element 6 have the same amount, the position P3 is usually not reached and at best only when the door is pressed strongly against the seal manually or by a vacuum inside the housing. The closing position can shift over the life of the seal 6 as the elastic deformability of the seal decreases due to aging and the magnetic force leads to a stronger compression of the seal. This shows an advantage of the invention, in which the non-contact or parallel movement of the first and second holding elements allows variability of the closing position and thus results in improved positional tolerance. The magnetic forces acting at positions P0, P1, P2 and P3 can be estimated by using the force/displacement curve of "Example 1" in FIG. 8.

Figure 2A:
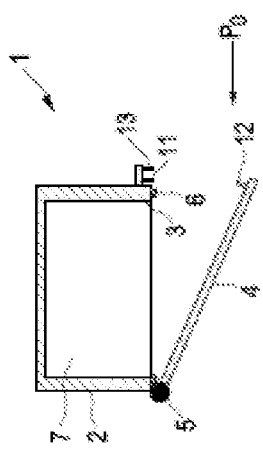
Figure 2B:
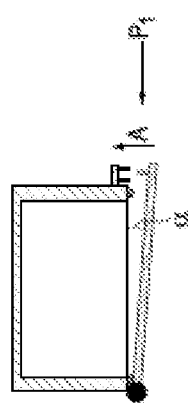
Figure 2C:
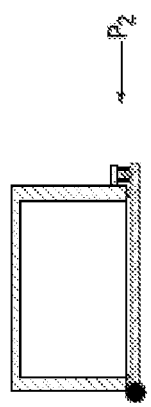
Figure 2D:
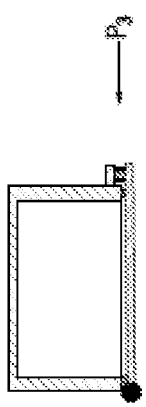

The arrangement of a holding device with a first, a second and a third holding element, which is shown in FIG. 2a, is also implemented in the embodiment of FIGS. 4 and 5. The first holding element 31 and the third holding element 33 are magnetic elements, here each consisting of a permanent magnet with the same polarity direction, which are attached to the carrier element 30 at a distance from each other. The support element 30a is attached to the outside of the housing 22 of an incubator 21. In the gap formed between the first holding element 31 and the third holding element 33, the second holding element 32 engages, which is also a permanent magnet with the same polarity as the first and the third permanent magnet, viewed in the closing position. The second magnetic element 32 is attached to a support element 30b, which is connected to the housing door 24.

An embodiment of the holding device with a holding force based on repulsive magnetic forces is illustrated using FIGS. 1e to 1h exemplary. FIGS. 1e to 1h show the operating principle of the laboratory cabinet device according to the invention for the preferred case that the magnetic force acting in the locking position causes the first holding element 11 and the second holding element 12' to repel. For this purpose the first permanent magnet 11 and the second permanent magnet 12' have opposite polarity directions M1< >M2, which results from the inversion of the relative position of north pole N and south pole S, compared to the permanent magnet 12 in FIG. 1a. The south pole is formed here by the upper side 12a of the plate-shaped permanent magnet 12', the north pole by its lower side 12b. Here a first relative position P1' of the first holding element 11 and of the second holding element 12' is provided, in which they exert a first repelling magnetic force F1 on each other. In a second relative position P2' of the first and the second holding elements, they exert a second repulsive magnetic force F2 on each other, which is, in particular, greater than the first magnetic force F1 and which is maximum at the reversal point shown here with directly opposite holding elements 11, 12' (reversal point). In the third relative position P3' of the first and second holding elements, they exert a third repulsive magnetic force F3 on each other, which is smaller than the second magnetic force F2. The first and second holding elements are arranged parallel and without contact with each other in such a way that when the housing door is closed they first reach the first relative position P1', then in the further course of the closing movement they reach the second relative position P2' and after that the closing position in which the third relative position P3' is present. By this arrangement, the housing door, preferably in the presence of the elastic element between the housing door and the housing, is forced into the closing position P3' by a repulsive magnetic force and thus is held in the closing position.

FIG. 6a shows a perspective exterior view of a holding device according to another embodiment, in the open position of the housing door. The construction of this holding device and its installation on the housing door and on the housing correspond to the arrangements shown in FIG. 4 and FIG. 5. The special feature of the example in FIGS. 6a to 6c is that the permanent magnets 31a and 33a of the first and third holding elements 31, 33 (attached to the housing) are arranged tilted in relation to the permanent magnet 32a of the second holding element 32 (attached to the housing door) inside the respective holding element 31, 33. The permanent magnets 31a and 33a are tilted relative to the permanent magnet 32a so that the magnetic axis M1 of the first permanent magnet 31a and the magnetic axis M3 of the third permanent magnet 33a are tilted relative to the magnetic axis M2 of the second permanent magnet 32a by the angle β=90°−α, wherein a is the angle of the magnetic axes M1 and M3 relative to the direction of movement A. A magnetic axis runs along the direction of polarity of the permanent magnet, which extends from the north pole to the south pole of the permanent magnet.

In FIG. 6c the closure is shown in cross-section as it is mounted on the laboratory cabinet 100 in a top view or, equally possible, in a bottom view. In particular, all holding elements are mounted so that their magnetic axes M1, M2 and M3 are perpendicular to the vertical, i.e. the direction of gravity, when the laboratory cabinet is used as intended. However, the magnetic axes M1, M2 and M3 could also be perpendicular to another axis direction, especially with the tilted arrangement of the permanent magnets shown here, or could be aligned differently. By tilting, the force-displacement curve is shaped in the desired way, as shown in the curve "Example 1" in FIG. 8. Here, the first, second and third permanent magnets 31a, 32a, 33a are each configured as a cuboid, plate-like component in which the direction of polarity is perpendicular to the main plane of the component, which runs parallel to the two largest outer surfaces. The magnetic axis M1, M2, M3 is always the normal to the main plane of the respective cuboid component.

FIG. 6b shows: the first holding element 31 is an essentially cuboidal component consisting of a socket 31b which encloses a cuboidal cavity in which the cuboidal permanent magnet 31a is enclosed and fixed, for example by gluing. The second holding element 32 is analogous to an essentially cuboidal component consisting of a socket 32b which encloses a cuboidal cavity in which the cuboidal permanent magnet 32a is enclosed and fixed, for example by gluing. The third holding element 33 is analogously an essentially cuboidal component consisting of a socket 33b which encloses a cuboidal cavity in which the cuboidal permanent magnet 33a is enclosed and fixed, for example by gluing. In FIG. 6c it can best be seen that the outer surfaces of the first, second and third holding elements 31, 32, 33 are parallel to each other in the closing position shown—in simple terms, the cuboid and plate-shaped holding elements are parallel to each other, while the permanent magnets M1 and M3 are tilted at the same angle β relative to M2. The parallel outer surfaces of the holding elements make it particularly easy to implement the feature that the first and second—or also the second and third—holding elements are arranged against each other in such a way that, when the housing door is closed, they reach the closing position by means of a closing movement by which the first and second holding elements are moved parallel to each other. However, this feature can also be achieved if the outer surfaces of the holding elements are not parallel to each other.

FIGS. 3a and 3b each show the first and second holding element of two holding devices, which can be used in a laboratory cabinet device according to further embodiments.

FIG. 7a shows a perspective exterior view of a holding device in the open position of the housing door, according to a further embodiment. The embodiment of the invention described here as "Example 2" (see FIG. 8, 9c) follows the principle shown in FIG. 3a with concentrically interlocking circular permanent magnets 131, 132 in the closed position. An example of a sliding door is shown in which the first holding element 130a is attached to the housing of a laboratory cabinet (not shown here) and the second holding element 130b to the sliding housing door (not shown here).

The sliding mechanism of the sliding door is represented here by the shown linear rail guide exemplary, which was used in the experiment to determine the force-displacement curve "Example 2" in FIG. 8. When closing this closure from the open position, as it is shown in FIGS. 7a to 7c, which corresponds to $P''_0$ in FIG. 8, a repelling magnetic force is first measured ($P''_1$ in FIG. 8). This repulsive magnetic force runs until the reversal point of a maximum. As the magnetic rings 131, 132 continue to approach, a point is passed at which there is no magnetic interaction (force=0), after which an attractive interaction starts immediately, and which runs to a maximum ($P''_3$). A suitable closing position, analogous to example 1, is position $P''_2$, in which the tightening force has not yet reached a maximum. This provides reserves for tolerance to door seals of different thicknesses, as has already been explained. The position $P''_3$ is therefore, normally not reached or at best only reached with thin seals of borderline thickness. As can be seen, the repelling force between $P''_0$ and $P''_2$ acts like a bolt, so that example 2 can also be called a magnetic bolt.

FIG. 8 also shows the force-displacement curve of a conventional clamp closure, in which the attractive force during approach is essentially proportional to the inverse square of the distance. On the last few millimeters of the approach until the magnets have adhered (FIG. 9a), the magnetic force increases almost abruptly, up to a high maximum. Such an arrangement causes mechanical shocks and vibrations, which can be avoided with the much more gentle operated holding devices according to the invention.

The invention claimed is:

1. Laboratory cabinet device (1; 21) for storing laboratory samples, comprising
   a housing (2; 22) with a housing opening (3) through which an interior (7) of the housing is accessible to the user,
      a housing door (4; 24) for closing the housing opening in a closed position,
      a holding device for holding the housing door in the closed position,
   wherein the holding device comprises a group of magnetically acting holding elements (11, 12, 13; 31, 32, 33) including a first holding element (11; 31) arranged on the housing and including a second holding element (12; 32) arranged on the housing door (4),
   characterised in that
   the first and second holding elements are arranged without contact and are configured to hold the housing door in the closed position by magnetic force,
   the first and second holding elements are arranged against each other in such a way that, when the housing door is closed, they reach the closing position by a closing movement by which the first and second holding elements are moved parallel or almost parallel to each other,
   the first and second holding elements each comprise a permanent magnet which has a magnetic axis extending along a magnetic north-south pole direction, and the closing movement on reaching the closing position is perpendicular to the magnetic axis or the closing movement on reaching the closing position runs at an angle α to the magnetic axis, wherein 70°<=α<90°, and
   the group of the holding elements comprises a third magnetically acting holding element which has a permanent magnet and is arranged on the housing or on the housing door and which, in addition to the first and second holding element, generates the magnetic force with which the housing door is held on the housing and in the closed position, wherein the first and the third holding element are spaced apart from one another in this way and are arranged with outer surfaces extending parallel to one another and which are opposite one another in the closed position, in such a way that a free space is formed between them, into which the second holding element engages in the closed position, or wherein the second and third holding elements are spaced apart from one another and are arranged with outer surfaces extending parallel to one another and which are opposite one another in the closed position, in such a way that a free space is formed between them, into which the first holding element engages in the closed position,
   wherein the first and second holding elements are arranged against each other in such a way that, when the housing door is closed, they first reach a first relative position (P1) and then reach the closing position in which there is a second relative position (P2), and the first and second holding elements exert a first attractive magnetic force (F1) on each other in the first relative position (P1) and exert a second attractive magnetic force (F2) on each other in the second relative position (P2), which is greater than the first magnetic force and
   wherein the first and second holding elements exert on each other in a third relative position (P3) a third attractive magnetic force (F3) greater than the second magnetic force, and
   a sealing device of the housing door or a frame of the housing opening comprises an elastic element, which is compressed in the closed position by the housing door by means of magnetic force, wherein the elastic element is being compressed more strongly in the third relative position (P3) than in the second relative position,
      wherein the closing position is the second relative position (P2) in which the second permanent magnet partially overlaps the first permanent magnet in the axial sliding direction and the permanent magnets thereof attract each other.

2. Laboratory cabinet device according to claim 1, wherein the first and second holding elements are spaced apart in the closed position so that their minimum spacing in the closed position is greater than zero.

3. Laboratory cabinet device according to claim 1, wherein the first and second holding elements have the same predetermined distance in the second and third relative positions, and the third magnetic force is the maximum achievable magnetic force between the first and second holding elements at this distance.

4. Laboratory cabinet device according to claim 1, wherein the group of holding elements comprises at least one cuboid permanent magnet whose north-south pole direction extends perpendicular to the largest area of the cuboid permanent magnet.

5. Laboratory cabinet device according to claim 4, wherein the at least one permanent magnet is part of a holding element of the group of holding elements, which comprises a socket, of which the at least one permanent magnet is enclosed, wherein this socket is not subjected to pressure from another holding element when the housing door is closed.

6. Laboratory cabinet device according to claim 1, which is a tempering cabinet for tempering laboratory samples.

7. Laboratory cabinet device according to claim 1, which is an incubator for cell cultures.

* * * * *